United States Patent [19]
Kobayashi et al.

[11] Patent Number: 5,783,647
[45] Date of Patent: Jul. 21, 1998

[54] 1,1,2,2-TETRAMETHYLPROPYLPEROXY ESTERS AND METHOD FOR PREPARING VINYL POLYMERS

[75] Inventors: Takashi Kobayashi; Tadashi Amano, both of Ibaraki-ken; Hideshi Kurihara, Kawasaki; Toshio Shinohara, Gunma-ken; Yoshitaka Okuno, Ibaraki-ken; Tohru Nishikawa, Aichi-ken, all of Japan

[73] Assignee: Shin-Etsu Chemical Co., Ltd., Tokyo, Japan

[21] Appl. No.: 566,509

[22] Filed: Dec. 4, 1995

[30] Foreign Application Priority Data

Dec. 15, 1994 [JP] Japan .................................. 6-333472
Dec. 15, 1994 [JP] Japan .................................. 6-333473

[51] Int. Cl.$^6$ .................. C08F 4/34; C08F 18/08; C08F 14/06; C08F 14/08
[52] U.S. Cl. ...................... 526/227; 526/343; 526/344; 526/319; 568/567
[58] Field of Search .................... 526/227, 343, 526/344, 319; 568/567

[56] References Cited

U.S. PATENT DOCUMENTS

| 3,446,831 | 5/1969 | Mageli et al. | 526/227 |
| 4,057,567 | 11/1977 | Friedman et al. | |
| 4,283,499 | 8/1981 | Howell | 526/227 |
| 5,357,011 | 10/1994 | Ohnishi et al. | 526/228 |

OTHER PUBLICATIONS

Chemical Abstracts 122:316 051 and R.N. 163 447–39–0, & JP A 06–316 611 (Nippon Oil & Fats).
Chemical Abstracts 115:50501, Columbus Ohio & JP A 03–020309 (Nippon Oil & Fats).

Primary Examiner—Joseph L. Schofer
Assistant Examiner—Wu C. Cheng
Attorney, Agent, or Firm—McAulay Fisher Nissen Goldberg & Kiel, LLP

[57] ABSTRACT

Novel 1,1,2,2-tetramethylpropylperoxy esters are provided. They are useful as a polymerization initiator in polymerizing vinyl chloride, vinylidene chloride and vinyl acetate monomers, with the advantage of completing polymerization within a short time.

9 Claims, No Drawings

1,1,2,2-TETRAMETHYLPROPYLPEROXY ESTERS AND METHOD FOR PREPARING VINYL POLYMERS

BACKGROUND OF THE INVENTION

1. Field of the Invention

This invention relates to novel 1,1,2,2-tetramethylpropylperoxy ester compounds which are useful as radical polymerization initiators for polymerizing vinyl monomers, typically vinyl chloride, vinylidene chloride and vinyl acetate monomers. It also relates to a method for preparing vinyl polymers, typically vinyl chloride, vinylidene chloride and vinyl acetate polymers of quality within a brief polymerization time.

2. Prior Art

In the manufacture of vinyl polymers such as vinyl chloride, vinylidene chloride and vinyl acetate polymers, it is desired to produce such polymers of quality in an efficient manner. There is an increasing demand for completing a polymerization process within a short time.

One approach to comply with such a demand in the polymerization of vinyl chloride monomers, for example, is to use polymerization initiators capable of affording a higher polymerization rate for accomplishing reaction within a short time. Exemplary polymerization initiators include tert-butylperoxypivalate, tert-butylperoxyneoheptanoate, tert-butylperoxyneodecanoate, tert-hexylperoxyneodecanoate, di-2-ethylhexylperoxydicarbonate, di-sec-butylperoxydicarbonate, 2,2'-azobis-2,4-dimethylvaleronitrile, 3,5,5-trimethylhexanoylperoxide, cumylperoxyneodecanoate, and isobutyrylperoxide.

Among these initiators, tert-butylperoxypivalate, tert-butylperoxyneoheptanoate, tert-butylperoxyneodecanoate, tert-hexylperoxyneodecanoate, 2,2'-azobis-2,4-dimethylvaleronitrile, and 3,5,5-trimethylhexanoylperoxide remain active and maintain a high polymerization reaction rate until an intermediate stage of polymerization, but experience a substantial drop of reaction rate in a later stage of polymerization after the internal pressure of the reactor starts to decline, leading to a long polymerization time, that is, failing to achieve the purpose of reducing the polymerization time. Di-2-ethylhexylperoxydicarbonate and di-sec-butylperoxydicarbonate maintain a relatively high polymerization reaction rate throughout the polymerization process, but prevents molded parts of the resulting polymers from being colored. Cumylperoxyneodecanoate remains active and maintains a high polymerization reaction rate until an intermediate stage of polymerization, but experiences a substantial drop of reaction rate in a later stage of polymerization after the internal pressure of the reactor starts to decline, leading to a long polymerization time, that is, failing to achieve the purpose of reducing the polymerization time. Additionally, since cumylperoxyneodecanoate has a phenyl group in its molecular structure, the resulting polymers are unsuitable for use in the medical field and evolve a smell when molded.

In connection with the manufacture of vinyl polymers, there is a desire to have a method for preparing a vinyl polymer which is improved in quality, especially colorability of polymer moldings and a hygienic aspect such as smell, the method being able to maintain a sufficiently high polymerization reaction rate throughout the process to complete the reaction within a short time.

SUMMARY OF THE INVENTION

An object of the present invention is to provide a novel 1,1,2,2-tetramethylpropylperoxy ester which is advantageously used as a polymerization initiator in the polymerization of a vinyl monomer so that a vinyl polymer of quality may be prepared within a short time.

Another object of the present invention is to provide an improved method for preparing a vinyl polymer of quality within a short time.

We have found that an 1,1,2,2-tetramethylpropylperoxy ester of formula (1) can be prepared by treating 1,1,2,2-tetramethylpropyl alcohol with aqueous hydrogen peroxide to form an alkylhydroperoxide of formula (2) and reacting it with an acid chloride of formula (3) according to the following reaction scheme.

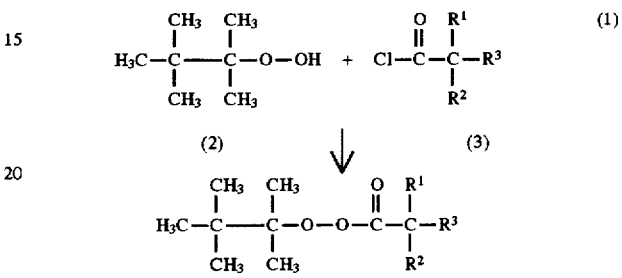

Note that $R^1$, $R^2$ and $R^3$ are independently selected from normal alkyl groups having 1 to 9 carbon atoms.

The 1,1,2,2-tetramethylpropylperoxy ester compounds of formula (1) are novel and useful as polymerization initiators in the polymerization of vinyl monomers. More particularly, when a vinyl monomer such as a vinyl chloride monomer, vinylidene chloride monomer or vinyl acetate monomer or a monomeric mixture mainly containing any of these monomers is polymerized, the polymerization reaction rate can be maintained high throughout the process by using a 1,1,2,2-tetramethylpropylperoxy ester of formula (1) as a polymerization initiator. The polymerization reaction rate can be maintained relatively high even in a later stage of polymerization after the internal pressure of the reactor starts to decline. Then polymerization can be completed within a short time. In addition, the resulting vinyl polymer as molded is improved in colorability and hygienic aspect. The present invention has overcome the above-mentioned problems of the prior art.

Therefore, the present invention also provides a method for preparing a vinyl polymer by adding a 1,1,2,2-tetramethylpropylperoxy ester of formula (1) as a polymerization initiator to a vinyl monomer charge for polymerization to proceed.

DETAILED DESCRIPTION OF THE INVENTION

In a first aspect, the present invention provides a novel 1,1,2,2-tetramethylpropylperoxy ester of the following general formula (1).

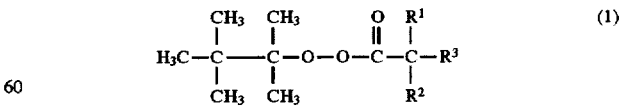

$R^1$, $R^2$ and $R^3$ which may be identical or different are selected from normal alkyl groups having 1 to 9 carbon atoms, for example, methyl, ethyl, n-propyl, n-butyl, n-pentyl, n-hexyl, n-heptyl, n-octyl, and n-nonyl groups. Preferably the alkyl groups represented by $R^1$, $R^2$ and $R^3$ have 3 to 11 carbon atoms in total because the esters have a low viscosity. Such a less viscous ester is advantageous in handling since it is easy to pump into the polymerization reactor. More preferably the alkyl groups represented by $R^1$, $R^2$ and $R^3$ have 3 to 8 carbon atoms in total.

Illustrative examples of the ester of formula (1) include 1,1,2,2-tetramethylpropylperoxypivalate, 1,1,2,2-tetramethylpropylperoxyneoheptanoate, and 1,1,2,2-tetramethylpropylperoxyneodecanoate. They are useful as the polymerization initiator.

The 1,1,2,2-tetramethylpropylperoxy ester of formula (1) is prepared by the following process. First, 1,1,2,2-tetramethylpropyl alcohol which is synthesized by a well-known technique (see Journal of the American Chemical Society/89:7/Mar. 29, 1967, for example) is treated with aqueous hydrogen peroxide and conc. sulfuric acid to form an alkylhydroperoxide of the following structural formula (2). This reaction is exothermic and is preferably carried out at room temperature.

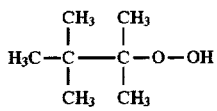

Next, the alkylhydroperoxide of formula (2) is reacting with an acid chloride of the following formula (3):

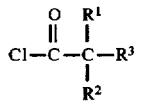

wherein $R^1$, $R^2$ and $R^3$ are as defined above (e.g., pivalic acid chloride, neohexanoic acid chloride, neoheptanoic acid chloride, neodecanoic acid chloride and neotridecanoic acid chloride) in the presence of a base catalyst (e.g., aqueous solution of potassium hydroxide) in an organic solvent (e.g., benzene, toluene, xylene, and n-hexane) while maintaining the reaction temperature below 20° C. The reaction solution is washed with water until it becomes neutral, and the organic layer is dried over anhydrous sodium sulfate. There is obtained a 1,1,2,2-tetramethylpropylperoxy ester of formula (1).

The peroxy esters of formula (1) are used as the polymerization initiator in the manufacture of vinyl polymers such as vinyl chloride polymers, vinylidene chloride polymers, vinyl acetate polymers, styrene polymers, acrylonitrile polymers, (meth)acrylate polymers, butadiene polymers and chloroprene polymers.

Among the 1,1,2,2-tetramethylpropylperoxy esters of formula (1), those having a 10-hour half-life temperature of 30° C. to 50° C. are preferred. The "10-hour half-life temperature" is the temperature at which the amount of a polymerization initiator in a 0.1 mol/liter benzene solution is reduced to one half in 10 hours.

When the peroxy esters of formula (1) are used as the polymerization initiator in the manufacture of vinyl polymers, the esters are preferably added to the polymerization system in an amount of 0.001 to 5 parts by weight, especially 0.01 to 0.3 part by weight per 100 parts by weight of the monomeric charge.

The method of preparing vinyl polymers by using the peroxy esters of formula (1) is more detailedly explained in the following.

The vinyl monomers used in the present invention include vinyl chloride, vinylidene chloride, vinyl acetate, styrene, acrylonitrile, acrylic acid, methacrylic acid, acrylate ester, metharylate ester, butadiene, and chloroprene monomers. They are used singly or in combination. Among them, vinyl chloride monomers, vinylidene chloride monomers, vinyl acetate monomers and monomeric mixtures mainly containing any of these monomers are preferably used for preparing vinyl chloride polymers, vinylidene chloride polymers and vinyl acetate polymers.

The vinyl chloride polymers include a vinyl chloride homopolymer and copolymers of vinyl chloride with other vinyl monomers, typically having a vinyl chloride content of at least 50% by weight, especially at least 70% by weight. The comonomers copolymerizable with vinyl chloride include α-olefins such as ethylene, propylene, 1-butene, 1-pentene, 1-hexene, 1-heptene, 1-octene, 1-nonene, 1-decene, 1-undecene, 1-dodecene, 1-tridecene, and 1-tetradecene; maleic acid and maleic anhydride; vinyl esters such as vinyl acetate; vinyl ethers such as lauryl vinyl ether and isobutyl vinyl ether; and vinylidene chloride.

The vinylidene chloride polymers include a vinylidene chloride homopolymer and copolymers of vinylidene chloride with other vinyl monomers, typically having a vinylidene chloride content of at least 50% by weight, especially at least 70% by weight. The comonomers copolymerizable with vinylidene chloride are the same as exemplified above (excluding vinylidene chloride itself).

The vinyl acetate polymers include a vinyl acetate homopolymer and copolymers of vinyl acetate with other vinyl monomers, typically having a vinyl acetate content of at least 50% by weight, especially at least 70% by weight. The comonomers copolymerizable with vinyl acetate are the same as exemplified above (excluding vinyl acetate itself).

According to the invention, the compound of formula (1) is used as a polymerization initiator when a vinyl monomer as exemplified above is polymerized. The compound of formula (1) used alone is effective for accomplishing brief polymerization reaction although the combined use of the compound of formula (1) with at least one polymerization initiator having a different activity is advantageous for maintaining a constant polymerization reaction rate throughout the polymerization process and reducing the polymerization time. More particularly, such improvements are achieved by using (A) a first polymerization initiator having a 10-hour half-life temperature of 30° C. to less than 40° C. and (B) a second polymerization initiator having a 10-hour half-life temperature of 40° C. to 70° C., especially 40° C. to 60° C. in combination. Such improvements have never been achieved with a mixture of conventional polymerization initiators.

The first polymerization initiators (A) having a 10-hour half-life temperature of 30° C. to less than 40° C. as measured in 0.1-mol/liter benzene solution include, for example, diacyl organic peroxides such as isobutyryl peroxide (10-hour half-life temperature 32.5° C., the same hereinafter), peroxyester organic peroxides such as cumylperoxyneodecanoate (36.6° C.), and peroxydicarbonate organic peroxides such as diallylperoxydicarbonate.

The second polymerization initiator (B) having a 10-hour half-life temperature of 40 ° C. to 70 ° C. as measured in 0.1-mol/liter benzene solution include, for example, diacyl organic peroxides such as 3,5,5-trimethylhexanoyl peroxide (59.5° C.) and lauroyl peroxide (62.0° C.); peroxyester organic peroxides such as tert-butylperoxypivalate (55.0° C.), tertbutylperoxyneoheptanoate (49.7° C.), tert-butylperoxyneodecanoate (46.5° C.), and tert-hexylperoxyneodecanoate (44.7° C.); peroxydicarbonate organic peroxides such as di-sec-butylperoxydicarbonate (45.0° C.) and di-2-ethylhexylperoxydicarbonate (43.5° C.); and azo compounds such as 2,2'-azobisisobutyronitrile (65.0° C.) and 2,2'-azobis-2,4-dimethylvaleronitrile (51.0°

C.). Preferred among these are 3,5,5-trimethylhexanoylperoxide, tert-butylperoxyneoheptanoate, tert-butylperoxyneodecanoate, and di-2-ethylhexylperoxydicarbonate.

According to the invention, the 1,1,2,2-tetramethylpropylperoxy ester of formula (1) is used as at least one of the first and second polymerization initiators (A) and (B). Preferably the difference in 10-hour half-life temperature between the first and second polymerization initiators (A) and (B) is at least 2° C., more preferably at least 5° C. A mixture of polymerization initiators (A) and (B) whose 10-hour half-life temperatures are approximate and differ only by less than 2° C. would be less effective for maintaining a constant polymerization reaction rate throughout the polymerization process and reducing the polymerization time.

For 100 parts by weight of the entire monomer charge, polymerization initiator (A) is preferably used in an amount of 0.001 to 0.5 part, especially 0.01 to 0.3 part by weight and polymerization initiator (B) is used in an amount of 0.001 to 0.5 part, especially 0.01 to 0.3 part by weight. The amount of polymerization initiators (A) and (B) combined is less than 0.5 part, especially less than 0.3 part by weight per 100 parts by weight of the entire monomer charge. On addition, the polymerization initiators are diluted with a solvent or dispersed in water to form an aqueous emulsion. After the reactor is charged with a monomer, the polymerization initiator is added to the reaction system by pumping the dilution or emulsion into the reactor.

Any desired polymerization technique may be used although radical polymerization techniques such as suspension polymerization, emulsion polymerization, solution polymerization and bulk polymerization are preferred, with the suspension polymerization being most preferred.

The suspension polymerization may be carried out in a well-known manner. The polymerization temperature is preferably 30° to 70° C., more preferably 40° to 65° C. The suspending agent used herein may be selected from conventional ones, for example, cellulose ethers such as methyl cellulose, hydroxyethyl cellulose, hydroxypropyl cellulose, and hydroxypropylmethyl cellulose, water or oil-soluble partially saponified polyvinyl alcohol, water-soluble polymers such as acrylic acid polymers and gelatin. They may be used alone or in admixture of two or more. In combination with the suspending agent, there can be used any of nonionic emulsifiers (e.g., sorbitan monolaurate, sorbitan trioleate, glycerin tristearate, and ethylene oxide-propylene oxide block copolymers) and anionic emulsifiers (e.g., polyoxyethylene sorbitan monolaurate, polyoxyethylene glycerin oleate, and sodium laurylsulfate). The suspending agent is preferably added in an amount of about 0.02 to 0.2% by weight of the monomer charge.

If desired, there may be added any of optional polymerization aids including a polymerization regulator, chain transfer agent, pH adjusting agent, gelation adjusting agent, anti-static agent, crosslinking agent, filler and anti-scaling agent.

There have been described novel 1,1,2,2-tetramethylpropylperoxy esters of formula (1) which are useful as a polymerization initiator in polymerizing vinyl monomers so that the polymerization reaction rate may be maintained high even in a later stage of polymerization after the internal pressure of the reactor starts to decline. Then polymerization can be completed within a short time. There is obtained a vinyl polymer of quality, from which are molded parts having improved colorability and hygienic property.

EXAMPLE

Examples of the present invention are given below by way of illustration and not by way of limitation. All parts are by weight.

Example 1

Preparation of 1,1,2,2-tetramethylpropylperoxypivalate

A 300-ml four-necked flask equipped with a stirrer, thermometer and dropping funnel was charged with 73.7 g of a 50% hydrogen peroxide aqueous solution. Stirring was started, the flask was kept at a temperature below 20° C. by water cooling, and 51.7 g of 98% conc. sulfuric acid was added dropwise to form a mixed acid. While the flask was cooled at a temperature of 0° to 5° C. with an ice bath, with stirring, 40 ml of a dichloromethane solution containing 42.9 g of 1,1,2,2-tetramethylpropyl alcohol which was previously synthesized according to Journal of the American Chemical Society/89:7/Mar. 29, 1967, was slowly added dropwise. At the end of addition, stirring was continued for a further 2 hours. The reaction solution was washed with pure water until the organic layer became neutral. The organic layer was dried over anhydrous sodium sulfate and distilled of the solvent, yielding 47.4 g of 1,1,2,2-tetramethylpropylhydroperoxide having structural formula (2).

Next, a 100-ml four-necked flask equipped with a stirrer, thermometer and dropping funnel was charged with 16.8 g of the thus obtained 1,1,2,2-tetramethylpropylhydroperoxide and then with 47.7 g of a 30% potassium hydroxide aqueous solution. The contents were stirred and mixed. While the flask was kept at a temperature of 0° to 5° C., with stirring, 11.1 g of pivalic acid chloride was added dropwise. Stirring was continued for a further 2 hours. The reaction solution was washed with water until neutral. The organic layer was dried over anhydrous sodium sulfate. The resulting compound was analyzed by iodometry to find an amount of 23.8 g and a yield of 91.7% (molar percent yield based on the hydroperoxide).

On analysis, the resulting compound was identified to be 1,1,2,2-tetramethylpropylperoxypivalate. The analytical results are shown below.

The compound had a 10-hour half-life temperature of 45.7° C. in a 0.1 mol/liter benzene solution and an active oxygen concentration of 7.40%.

Exact MASS: m/z: 216.3211 $C_{12}O_3H_{12}$: 216.3208 (calcd.)

NMR spectrum:

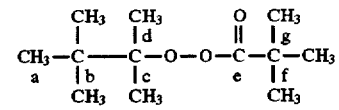

| $^1$H-NMR (acetone-d6) | |
|---|---|
| H | δ (ppm) |
| a | 1.01 (s, 9H) |
| d | 1.26 (s, 6H) |
| g | 1.23 (s, 9H) |

| $^{13}$C-NMR (acetone-d6) | |
|---|---|
| C | δ (ppm) |
| a | 26.07 |
| b | 38.30 |
| c | 86.64 |

-continued

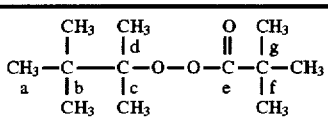

| | |
|---|---|
| d | 20.80 |
| e | 175.10 |
| f | 39.32 |
| g | 27.45 |

IR (neat): v/cm$^{-1}$ 1768 (C=O stretching) 1095 (C—O stretching) 850 (O—O stretching)

Example 2
Preparation of 1,1,2,2-tetramethylpropylperoxyneoheptanoate

The procedure of Example 1 was repeated except that neoheptanoic acid chloride was used instead of pivalic acid chloride, obtaining an end compound in an amount of 21.3 g and a yield of 72.5%.

On analysis, the resulting compound was identified to be 1,1,2,2-tetramethylpropylperoxyneoheptanoate. It had a 10-hour half-life temperature of 40.6° C. in a 0.1 mol/liter benzene solution and an active oxygen concentration of 6.55%. The analytical results are shown below.

Exact MASS: m/z: 244.3743 $C_{12}O_3H_{12}$: 244.3745 (calcd.)

NMR spectrum:

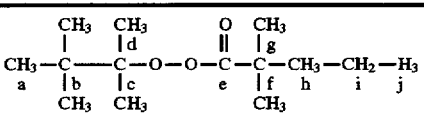

| $^1$H-NMR (acetone-d6) | |
|---|---|
| H | δ (ppm) |
| a | 1.03 (s, 9H) |
| d | 1.20 (s, 6H) |
| g | 1.24 (s, 6H) |
| h | 1.32–1.35 (m, 2H) |
| i | 1.50–1.57 (m, 2H) |
| j | 0.87 (t, 3H, J=7 Hz) |

| $^{13}$C-NMR (acetone-d6) | |
|---|---|
| C | δ (ppm) |
| a | 26.07 |
| b | 38.31 |
| c | 86.66 |
| d | 20.81 |
| e | 174.80 |
| f | 43.10 |
| g | 25.50 |
| h | 43.82 |
| i | 18.90 |
| j | 14.76 |

IR (neat): v/cm$^{-1}$ 1765 (C=O stretching) 1093 (C—O stretching) 851 (O—O stretching)

Example 3
Preparation of 1,1,2,2-tetramethylpropylperoxyneodecanoate

The procedure of Example 1 was repeated except that neodecanoic acid chloride was used instead of pivalic acid chloride, obtaining an end compound in an amount of 23.2 g and a yield of 67.5%.

On analysis, the resulting compound was identified to be 1,1,2,2-tetramethylpropylperoxyneodecanoate. It had a 10-hour half-life temperature of 39.0° C. in a 0.1 mol/liter benzene solution and an active oxygen concentration of 5.59%. The analytical results are shown below.

Exact MASS: m/z: 286.4549 $C_{12}O_3H_{12}$: 286.4552 (calcd.)

NMR spectrum:

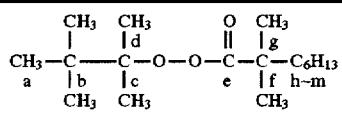

| $^1$H-NMR (acetone-d6) | |
|---|---|
| H | δ (ppm) |
| a | 1.02 (s, 9H) |
| d | 1.17 (s, 6H) |
| g–m | 0.68–1.55 (m, 19H) |

Identification by $^{13}$C-NMR was impossible because the neodecanoic acid was a mixture of isomers.

IR (neat):
v/cm$^{-1}$ 1770 (C=O stretching) 1095 (C—O stretching) 850 (O—O stretching)

The 10-hour half-life temperature and active oxygen concentration were measured as follows.

Measurement of active oxygen concentration of polymerization initiator by iodometry This measurement was in accord with "Organic Peroxides, Their Chemistry and Industrial Use", edited by Organic Peroxide Research Group, Kagaku Kogyo K.K., 1952.

A 300-ml Erlenmeyer flask with ground stopper was charged with 30 ml of benzene. The flask was purged with carbon dioxide by passing it at a rate of about 2.5 liter/min. for about 30 seconds. A sample (1.5 to 1.8 meq) was precisely weighed and admitted into the flask. To the flask, 2 ml of a saturated sodium iodide aqueous solution was added and then 70 ml of an acetic acid aqueous solution of ferric chloride (0.0002% $FeCl_3.6H_2O$ ) was added. The contents were fully mixed and allowed to stand in the dark for 15 minutes. About 80 ml of pure water was added to the mixture, which was titrated with 0.1N sodium thiosulfate solution until the mixture became colorless. A blank test was separately carried out under the same conditions.

Measurement of 10-hour half-life temperature of polymerization initiator

A polymerization initiator or peroxide was dissolved in benzene solvent to prepare a solution having a peroxide concentration of 0.1 mol/l. The solution was sealingly contained in a glass tube purged with nitrogen. The glass tube was immersed in a constant temperature bath set at a predetermined temperature. Under the conditions, the polymerization initiator was thermally decomposed. The active oxygen concentration was measured by the above-mentioned procedure to determine a change with time of the concentration of undecomposed polymerization initiator, from which a decomposition rate constant at the set temperature is determined.

Polymerization initiator thermal decomposition equation $$[I]=[I]_0 \cdot exp(-K \cdot t) \tag{i}$$

[I]: polymerization initiator concentration
[I]$_0$: initial polymerization initiator concentration
K: decomposition rate constant at the set temperature
t: time By the above-mentioned procedure, K is determined for four different temperatures. These data are plotted in Arrhenius' diagram with ln(K) on the ordinate and 1/(R·T) on the abscissa. The activation energy (Ea) of the polymerization initiator is determined from the gradient and the frequency factor (A) is determined from a y segment.

Decomposition rate constant equation $$K = A \cdot \exp(-Ea/(R \cdot T)) \quad \text{(ii)}$$

It is modified as below.

$$\ln(K) = \ln(A) - Ea/(R \cdot T)$$

A: frequency factor of polymerization initiator
Ea: activation energy of polymerization initiator
R: gas constant
T: temperature The temperature at which the concentration of polymerization initiator is reduced to ½ in 10 hours, that is, 10-hour half-life temperature T is determined by assuming $[I] = ½[I]_0$ and t=10 for equation (i) and substituting therein equation (ii) wherein A and Ea have known values. Example 4

A stainless steel polymerization reactor having an internal volume of 2 liters and a coil for adjusting the internal temperature was charged with 1250 g of deionized water and 50 g of deionized water having dissolved therein 0.36 g of water-soluble partially saponified polyvinyl alcohol and 0.24 g of water-soluble cellulose ether. The reactor was evacuated until an internal pressure of 50 mmHg absolute was reached. The reactor was further charged with 405 g of vinyl chloride monomer (VCM). With stirring, the reactor was heated by passing hot water through the coil until an internal temperature of 57° C. was reached. At this point, a 25% isoparaffin solution containing 1.62 g of 1,1,2,2-tetramethylpropylperoxypivalate (TMPV), which corresponded 0.100% by weight of TMPV based on VCM, was injected into the reactor by means of a syringe, thereby initiating polymerization. At the same time, cooling water was passed through the coil to keep the internal temperature (or polymerization temperature) at 57° C. to continue polymerization.

At the time when the internal pressure of the reactor declined to 4.5 kgf/cm², 0.225 g of a 20% methanol solution of bisphenol A was injected into the reactor by means of a syringe, thereby interrupting polymerization. After the exhaust gas (unreacted monomer) was recovered, the vinyl chloride polymer slurry was taken out, dewatered, and dried, collecting 366 g (yield 90.4%) of the vinyl chloride polymer.

Example 5

A vinyl chloride polymer was prepared by repeating the procedure of Example 4 except that 0.080% by weight based on VCM of TMPV and 0.026% by weight based on VCM of 1,1,2,2-tetramethylpropylperoxyneodecanoate (TMND) was used instead of 0.100% by weight based on VCM of TMPV. Note that the TMPM and the TMND added was in an equimolar amount to the TMPM in Example 4.

Example 6

A vinyl chloride polymer was prepared by repeating the procedure of Example 4 except that a mixture of 0.038% by weight based on VCM of TMPV and 0.030% by weight based on VCM of cumylperoxyneodecanoate (CND) was used instead of 0.100% by weight based on VCM of TMPV, and polymerization was interrupted when the internal pressure of the reactor declined to 5.5 kgf/cm².

Example 7

A vinyl chloride polymer was prepared by repeating the procedure of Example 4 except that 0.070% by weight based on VCM of 1,1,2,2-tetramethylpropylperoxyneodecanoate (TMND) was used instead of 0.100% by weight based on VCM of TMPV, the polymerization temperature was 54° C., and polymerization was interrupted when the internal pressure of the reactor declined to 4.2 kgf/cm².

Example 8

A vinyl chloride polymer was prepared by repeating the procedure of Example 4 except that a mixture of 0.020% by weight based on VCM of 1,1,2,2-tetramethylpropylperoxyneodecanoate (TMND) and 0.050% by weight based on VCM of tert-butylperoxyneodecanoate (BND) was used instead of 0.100% by weight based on VCM of TMPV, and polymerization was interrupted when the internal pressure of the reactor declined to 6.4 kgf/cm².

Example 9

A vinyl chloride polymer was prepared by repeating the procedure of Example 4 except that a mixture of 0.020% by weight based on VCM of 1,1,2,2-tetramethylpropylperoxyneodecanoate (TMND) and 0.090% by weight based on VCM of tert-butylperoxyneodecanoate (BND) was used instead of 0.100% by weight based on VCM of TMPV, the polymerization temperature was 51° C., and polymerization was interrupted when the internal pressure of the reactor declined to 6.4 kgf/cm².

Example 10

A vinyl chloride-vinyl acetate copolymer was prepared by repeating the procedure of Example 4 except that the reactor was charged with 405 g of a mixture of VCM and vinyl acetate monomer (weight ratio 9/1), 0.090% by weight based on the monomer charge of 1,1,2,2-tetramethylpropylperoxyneoheptanoate (TMHP) was used instead of 0.100% by weight based on VCM of TMPV, the polymerization temperature was 57° C., and polymerization was interrupted when the internal pressure of the reactor declined to 4.2 kgf/cm².

Comparative Example 1

A vinyl chloride polymer was prepared by repeating the procedure of Example 4 except that 0.113% by weight based on VCM of tert-butylperoxyneodecanoate (BND) was used instead of 1,1,2,2-tetramethylpropylperoxypivalate (TMPV). Note that the BND added was in an equimolar amount to TMPV in Example 4.

Comparative Example 2

A vinyl chloride polymer was prepared by repeating the procedure of Example 4 except that 0.094% by weight based on VCM of tert-butylperoxyneoheptanoate (BNH) was used instead of 1,1,2,2-tetramethylpropylperoxypivalate (TMPV). Note that the BNH added was in an equimolar amount to TMPV in Example 4.

Comparative Example 3

A vinyl chloride polymer was prepared by repeating the procedure of Example 4 except that 0.160% by weight based on VCM of di-2-ethylhexylperoxydicarbonate (EHP) was used instead of 1,1,2,2-tetramethylpropylperoxypivalate (TMPV). Note that the EHP added was in an equimolar amount to TMPV in Example 4.

Comparative Example 4

A vinyl chloride polymer was prepared by repeating the procedure of Example 6 except that 0.043% by weight based on VCM of tert-butylperoxyneodecanoate (BND) was used instead of 1,1,2,2-tetramethylpropylperoxypivalate (TMPV). Note that the BND added was in an equimolar amount to TMPV in Example 6.

Comparative Example 5

A vinyl chloride polymer was prepared by repeating the procedure of Example 6 except that 0.061% by weight based on VCM of di-2-ethylhexylperoxydicarbonate (EHP) was used instead of 1,1,2, 2-tetramethylpropylperoxypivalate (TMPV). Note that the EHP added was in an equimolar amount to TMPV in Example 6.

Comparative Example 6

A vinyl chloride polymer was prepared by repeating the procedure of Example 6 except that 0.041% by weight based on VCM of di-sec-butylperoxydicarbonate (SBP) was used instead of 1,1,2,2-tetramethylpropylperoxypivalate (TMPV). Note that the SBP added was in an equimolar amount to TMPV in Example 6.

Comparative Example 7

A vinyl chloride polymer was prepared by repeating the procedure of Example 7 except that 0.075% by weight based on VCM of cumylperoxyneodecanoate (CND) was used instead of 1,1,2,2-tetramethylpropylperoxyneodecanoate (TMND) and polymerization was interrupted when the internal pressure of the reactor declined to 6.6 kgf/cm$^2$. Note that the CND added was in an equimolar amount to TMND in Example 7.

Comparative Example 8

A vinyl chloride polymer was prepared by repeating the procedure of Example 8 except that 0.067% by weight based on VCM of tert-butylperoxyneodecanoate (BND) was used instead of the mixture of 0.020% by weight based on VCM of 1,1,2,2-tetramethylpropylperoxyneodecanoate (TMND) and 0.050% by weight based on VCM of tert-butylperoxyneodecanoate (BND). Note that the BND added was in an equimolar amount to TMND+BND in Example 8.

Comparative Example 9

A vinyl chloride polymer was prepared by repeating the procedure of Example 8 except that 0.020% by weight based on VCM of cumylperoxyneodecanoate (CND) was used instead of 1,1,2,2-tetramethylpropylperoxyneodecanoate (TMND). Note that the CND added was in an equimolar amount to TMND in Example 8.

Comparative Example 10

A vinyl chloride polymer was prepared by repeating the procedure of Example 9 except that 0.020% by weight based on VCM of cumylperoxyneodecanoate (CND) was used instead of 1,1,2,2-tetramethylpropylperoxyneodecanoate (TMND). Note that the CND added was in an equimolar amount to TMND in Example 9.

Comparative Example 11

A vinyl chloride-vinyl acetate copolymer was prepared by repeating the procedure of Example 10 except that 0.090% by weight based on the monomer charge of tert-butylperoxyneodecanoate (BND) was used instead of 1,1,2, 2-tetramethylpropylperoxyneoheptanoate (TMHP). Note that the BND added was in an equimolar amount to TMHP in Example 10.

Comparative Example 12

A vinyl chloride-vinyl acetate copolymer was prepared by repeating the procedure of Example 10 except that 0.139% by weight based on the monomer charge of di-2-ethylhexylperoxydicarbonate (EHP) was used instead of 1,1,2,2-tetramethylpropylperoxyneoheptanoate (TMHP). Note that the EHP added was in an equimolar amount to TMHP in Example 10.

The vinyl chloride polymers prepared in Examples 4–10 and Comparative Examples 1 to 12 were examined for initial coloring. The results are shown in Table 1.

Initial coloring (IC) test

With 100 parts by weight of a vinyl chloride polymer were blended 1 part by weight of tin laurate, 0.5 part by weight of a cadmium stabilizer, and 50 parts by weight of dioctyl phthalate. The blend was milled in a twin roll mill at 160° C. for 5 minutes and formed into a sheet of 0.8 mm thick. The sheet was cut into sections which were stacked one on top of the other. The stack was placed in a mold of 4×4×1.5 cm where it was heat compression molded at 160° C. and 65–70 kgf/cm$^2$ to form a sample. By analyzing the sample using a photoelectric calorimeter (manufactured by Nihon Denshoku Kogyo K.K.), a lightness index L and values of a and b in Hunter's color difference equation were determined as prescribed in JIS Z-8730 (1980).

It is understood that for the vinyl chloride-vinyl acetate copolymers of Example 6 and Comparative Examples 11 and 12, the initial coloring measurement was done under the same conditions as above except that 30 parts by weight of dioctyl phthalate was blended, the roll mill temperature was 120° C., and the mold was dimensioned 4×4×0.5 cm.

The samples were rated "◉" for excellent, "○" for good, "Δ" for fair, and "X" for poor.

The terms used in Table 1 are defined below. Polymerization started when the polymerization initiator was admitted. This is the start of polymerization. The reaction system is under the initial internal pressure at this point. At a certain time after the start of polymerization, the internal pressure of the reactor began declining. Polymerization was interrupted when the (predetermined) final internal pressure was reached. This is the end of polymerization. The "time before pressure decline" is a duration from the start of polymerization to the time when the internal pressure began declining. The "pressure decline rate" is a rate of pressure decline from the time when the internal pressure began declining to the end of polymerization. The "time from pressure decline to end" is a duration from the time when the reactor internal pressure began declining to the end of polymerization.

It is understood that for the vinyl chloride-vinyl acetate copolymers of Example 6 and Comparative Examples 11 and 12, the "time before pressure decline" is zero. This means that unlike the vinyl chloride homopolymers, the reactor internal pressure gradually declined from the start of polymerization. In this case, the "pressure decline rate" is a rate of pressure decline from the start to the end of polymerization.

With respect to the polymerization initiators, their abbreviation and 10-hour half-life temperature (in 0.1 mol/liter benzene solution) are listed below.

| Abbreviation | Name | 10-hour half-life temperature |
|---|---|---|
| TMPV | 1,1,2,2-tetramethylpropyl-peroxypivalate | 45.7° C. |
| TMHP | 1,1,2,2-tetramethylpropyl-peroxyneoheptanoate | 40.6° C. |
| TMND | 1,1,2,2-tetramethylpropyl-peroxyneodecanoate | 39.0° C. |
| BND | tert-butylperoxyneodecanoate | 46.5° C. |
| BNH | tert-butylperoxyneoheptanoate | 52.1° C. |
| EHP | di-2-ethylhexylperoxydicarbonate | 43.5° C. |
| SBP | di-sec-butylperoxydicarbonate | 45.0° C. |
| CND | cumylperoxyneodecanoate | 36.6° C. |

TABLE 1

| | Example | | Comparative Example | | | Example | Comparative Example | | |
|---|---|---|---|---|---|---|---|---|---|
| | 4 | 5 | 1 | 2 | 3 | 6 | 4 | 5 | 6 |
| Polymerization initiator | | | | | | | | | |
| Type | TMPV | TMPV | BND | BNH | EHP | TMPV | BND | EHP | SBP |
| Amount, wt % | 0.100 | 0.080 | 0.113 | 0.094 | 0.160 | 0.038 | 0.043 | 0.061 | 0.041 |
| Amount, mol % | 4.62 × 10$^{-4}$ | 3.70 × 10$^{-4}$ | 4.62 × 10$^{-4}$ | 4.62 × 10$^{-4}$ | 4.62 × 10$^{-4}$ | 1.76 × 10$^{-4}$ | 1.76 × 10$^{-4}$ | 1.76 × 10$^{-4}$ | 1.76 × 10$^{-4}$ |
| Type | — | TMND | — | — | — | CND | CND | CND | CND |
| Amount, wt % | — | 0.026 | — | — | — | 0.030 | 0.030 | 0.030 | 0.030 |
| Amount, mol % | — | 0.91 × 10$^{-4}$ | — | — | — | 0.98 × 10$^{-4}$ | 0.98 × 10$^{-4}$ | 0.98 × 10$^{-4}$ | 0.98 × 10$^{-4}$ |
| Polymerization temperature (°C.)/ Initial internal pressure (kgf/cm$^2$) | 57.0/8.6 | 57.0/8.6 | 57.0/8.6 | 57.0/8.6 | 57.0/8.6 | 57.0/8.6 | 57.0/8.6 | 57.0/8.6 | 57.0/8.6 |
| Pressure decline rate (kgf/cm$^2$/hr.) | 8.5 | 9.5 | 2.5 | 2.8 | 4.7 | 5.2 | 1.4 | 2.5 | 2.2 |
| Final internal pressure (kgf/cm$^2$) | 4.5 | 4.5 | 4.5 | 4.5 | 4.5 | 5.5 | 5.5 | 5.5 | 5.5 |
| Time before pressure decline (min.) | 123 | 108 | 133 | 148 | 103 | 188 | 193 | 159 | 176 |
| Time from pressure decline to end (min.) | 29 | 26 | 97 | 88 | 52 | 36 | 134 | 74 | 84 |
| Overall polymerization time (min.) | 152 | 134 | 230 | 236 | 155 | 224 | 327 | 233 | 260 |
| Yield (%) | 90.4 | 90.4 | 90.3 | 90.2 | 90.2 | 87.5 | 87.2 | 87.4 | 87.5 |
| Initial coloring | | | | | | | | | |
| L value | 70.4 | 70.4 | 70.1 | 70.4 | 67.5 | 70.6 | 70.4 | 68.3 | 68.0 |
| a value | −1.3 | −1.3 | −1.3 | −1.4 | −1.0 | −1.4 | −1.3 | −1.1 | −1.1 |
| b value | 11.8 | 11.7 | 11.9 | 11.8 | 15.9 | 11.5 | 11.7 | 14.5 | 14.8 |
| Rating | ⊚ | ⊚ | ⊚ | ⊚ | x | ⊚ | ⊚ | x | x |

| | Example | Comparative Example | Example | Comparative Example | Example | Comparative Example | Example | Comparative Example | |
|---|---|---|---|---|---|---|---|---|---|
| | 7 | 7 | 8 | 8 | 9 | 9 | 10 | 10 | 11 | 12 |
| Polymerization initiator | | | | | | | | | | |
| Type | TMND | CND | TMND | BND | CND | TMND | CND | TMHP | BND | EHP |
| Amount, wt % | 0.070 | 0.075 | 0.020 | 0.067 | 0.021 | 0.020 | 0.021 | 0.090 | 0.090 | 0.139 |
| Amount, mol % | 2.44 × 10$^{-4}$ | 2.44 × 10$^{-4}$ | 0.70 × 10$^{-4}$ | 2.74 × 10$^{-4}$ | 0.70 × 10$^{-4}$ | 0.70 × 10$^{-4}$ | 0.70 × 10$^{-4}$ | 4.01 × 10$^{-4}$ | 4.01 × 10$^{-4}$ | 4.01 × 10$^{-4}$ |
| Type | — | — | BND | — | BND | BND | BND | — | — | — |
| Amount, wt % | — | — | 0.050 | — | 0.050 | 0.090 | 0.090 | — | — | — |
| Amount, mol % | — | — | 2.04 × 10$^{-4}$ | — | 2.04 × 10$^{-4}$ | 3.68 × 10$^{-4}$ | 3.68 × 10$^{-4}$ | — | — | — |
| Polymerization temperature (°C.)/ Initial internal pressure (kgf/cm$^2$) | 54.0/7.9 | 54.0/7.9 | 57.0/8.6 | 57.0/8.6 | 57.0/8.6 | 51.0/7.2 | 51.0/7.2 | 57.0/8.5 | 57.0/8.5 | 57.0/8.5 |
| Pressure decline rate (kgf/cm$^2$/hr.) | 9.6 | 1.0 | 4.4 | 1.6 | 1.8 | 4.0 | 1.7 | 1.4 | 0.9 | 1.3 |
| Final internal pressure (kgf/cm$^2$) | 4.2 | 6.6 | 6.4 | 6.4 | 6.4 | 5.0 | 5.0 | 4.2 | 4.2 | 4.2 |
| Time before pressure decline (min.) | 134 | 204 | 166 | 201 | 187 | 193 | 213 | 0 | 0 | 0 |
| Time from pressure decline to end (min.) | 23 | 76 | 30 | 82 | 74 | 33 | 79 | 181 | 288 | 202 |
| Overall polymerization time (min.) | 157 | 280 | 196 | 283 | 261 | 226 | 292 | 181 | 288 | 202 |
| Yield (%) | 90.0 | 81.3 | 84.7 | 84.7 | 84.5 | 86.1 | 86.1 | 88.4 | 88.2 | 88.3 |
| Initial coloring | | | | | | | | | | |
| L value | 70.2 | 70.4 | 70.4 | 70.2 | 70.3 | 70.8 | 70.0 | 82.8 | 82.6 | 79.5 |

TABLE 1-continued

| a value | −1.2 | −1.4 | −1.3 | −1.2 | −1.3 | −1.2 | −1.2 | −0.3 | −0.3 | −0.1 |
|---|---|---|---|---|---|---|---|---|---|---|
| b value | 12.0 | 11.8 | 11.7 | 11.9 | 11.9 | 11.9 | 12.1 | 5.9 | 6.2 | 8.7 |
| Rating | ◎ | ◎ | ◎ | ◎ | ◎ | ◎ | ◎ | ◎ | ◎ | x |

It is evident from Table 1 that when a vinyl monomer is polymerized using 1,1,2,2-tetramethylpropylperoxy esters according to the invention, specifically TMPV, TMHP and TMND alone as the polymerization initiator (Examples 4, 7 and 10), polymerization reaction can be completed within a short time and parts molded from the resulting polymers are improved in colorability. When a vinyl monomer is polymerized using a 1,1,2,2-tetramethylpropylperoxy ester according to the invention, specifically TMPV, TMHP or TMND in combination with another polymerization initiator having a different 10-hour half-life temperature (Examples 5, 6, 8 and 9), these combinations achieve a significant reduction of polymerization time which has been never achieved by a combination of conventional polymerization initiators while maintaining the improved initial colorability of the resulting polymers.

Japanese Patent Application Nos. 333472/1994 and 333473/1994 are incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A 1,1,2,2-tetramethylpropylperoxy ester of the following general formula (1):

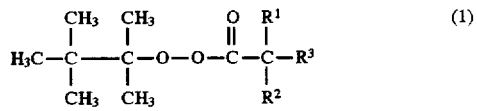

(1)

wherein $R^1$, $R^2$ and $R^3$ are independently selected from normal alkyl groups having 1 to 9 carbon atoms.

2. The ester of claim 1 wherein the groups represented by $R^1$, $R^2$ and $R^3$ have up to 11 carbon atoms in total.

3. The ester of claim 2 wherein the groups represented by $R^1$, $R^2$ and $R^3$ have up to 8 carbon atoms in total.

4. A method for preparing a vinyl polymer comprising the step of polymerizing a vinyl monomer in the presence of a 1,1,2,2-tetramethylpropylperoxy ester of the following general formula (1):

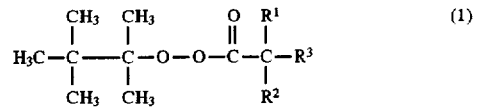

(1)

wherein $R^1$, $R^2$ and $R^3$ are independently selected from normal alkyl groups having 1 to 9 carbon atoms.

5. The method of claim 4, wherein the vinyl monomer is vinyl chloride, vinylidene chloride, vinyl acetate or a monomeric mixture mainly containing any of these monomers.

6. The method of claim 4 wherein the groups represented by $R^1$, $R^2$ and $R^3$ in formula (1) have up to 11 carbon atoms in total.

7. The method of claim 5 wherein the groups represented by $R^1$, $R^2$ and $R^3$ in formula (1) have up to 8 carbon atoms in total.

8. The method of claim 4 wherein the polymer obtained is a vinyl chloride polymer.

9. The method of claim 4 wherein the vinyl monomer is vinyl chloride, vinylidene chloride, vinyl acetate or a monomeric mixture mainly containing any of these monomers, and as a polymerization initiator a mixture of a first polymerization initiator having a 10-hour half-life temperature of 30° C. to less than 40° C. and a second polymerization initiator having a 10-hour half-life temperature of 40° C. to 70° C., at least one of the first and second polymerization initiators being the 1,1,2,2-tetramethylpropylperoxy esters of formula (1) is used.

* * * * *